US010524707B2

(12) United States Patent
Li et al.

(10) Patent No.: US 10,524,707 B2
(45) Date of Patent: Jan. 7, 2020

(54) SYSTEM AND METHOD FOR PHOTOLUMINESCENCE DETECTION

(71) Applicant: THE GENERAL HOSPITAL CORPORATION, Boston, MA (US)

(72) Inventors: Zongxi Li, Cambridge, MA (US); Conor L. Evans, Charlestown, MA (US); Alexander J. Nichols, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 344 days.

(21) Appl. No.: 15/114,951

(22) PCT Filed: Feb. 2, 2015

(86) PCT No.: PCT/US2015/014065
§ 371 (c)(1),
(2) Date: Jul. 28, 2016

(87) PCT Pub. No.: WO2015/163957
PCT Pub. Date: Oct. 29, 2015

(65) Prior Publication Data
US 2016/0338631 A1  Nov. 24, 2016

Related U.S. Application Data

(60) Provisional application No. 61/934,487, filed on Jan. 31, 2014.

(51) Int. Cl.
*A61B 5/1455* (2006.01)
*A61B 5/1477* (2006.01)
(Continued)

(52) U.S. Cl.
CPC ........ *A61B 5/14556* (2013.01); *A61B 5/1477* (2013.01); *A61B 5/7475* (2013.01); *A61F 13/00004* (2013.01)

(58) Field of Classification Search
CPC .............. A61B 5/1455; A61B 5/14551; A61B 5/14552; A61B 5/14556; A61B 5/1477;
(Continued)

(56) References Cited

U.S. PATENT DOCUMENTS 4,947,850 A    8/1990  Vanderkooi et al.
5,127,405 A *  7/1992  Alcala ................ A61B 5/14555
                                                600/342
(Continued)

FOREIGN PATENT DOCUMENTS

JP    2001027605 A    1/2001
WO    2006026396 A2   3/2006
WO    2014/011724     1/2014

OTHER PUBLICATIONS

European Patent Office, Extended European Search Report, Application No. 15783035.7, dated Sep. 11, 2017.
(Continued)

*Primary Examiner* — Eric F Winakur
*Assistant Examiner* — Chu Chuan Liu
(74) *Attorney, Agent, or Firm* — Quarles & Brady LLP

(57) ABSTRACT

In one aspect, the present disclosure provides a system A system, including a light source, a detector, and a controller in electrical communication with the light source and the detector. The controller is configured to execute a program stored in the controller to trigger the light source to emit a first pulse of light having a first pulse duration for illumination of a target, actuate the detector after a first delay time following emission of the first pulse of light to begin detecting a first signal from the target for a first detection time, and repeat the steps of triggering the light source and actuating the detector at least once, varying for each repetition at least one of the first pulse duration, the first delay time, and the first detection time.

28 Claims, 12 Drawing Sheets

(51) Int. Cl.
*A61B 5/00* (2006.01)
*A61F 13/00* (2006.01)

(58) Field of Classification Search
CPC .... A61B 5/7475; A61B 5/443; A61B 5/14542
See application file for complete search history.

(56) References Cited

U.S. PATENT DOCUMENTS

| | | | |
|---|---|---|---|
| 5,128,708 | A | 7/1992 | Murayama et al. |
| 6,252,650 | B1 | 6/2001 | Nakamura |
| 7,215,421 | B2 | 5/2007 | Kotani |
| 2002/0123781 | A1 | 9/2002 | Shanks et al. |
| 2007/0018116 | A1 | 1/2007 | Lustenberger et al. |
| 2009/0082650 | A1* | 3/2009 | Wilson .............. A61B 5/1455 600/323 |
| 2012/0209125 | A1 | 8/2012 | Davis et al. |
| 2012/0289899 | A1 | 11/2012 | Wu |
| 2015/0182166 | A1* | 7/2015 | Evans .............. A61B 5/6833 600/317 |

OTHER PUBLICATIONS

International Search Report and Written Opinion dated Oct. 23, 2015 for International Application No. PCT/US2015/014065.

Chu, et al., 2D Full-Field Measurement of Oxygen Concentration Based on the Phase Fluorometry Technique that Uses the Four-Frame Integrating-Bucket Method, Sensors and Actuators B, 2010, 147:310-315.

Holst, et al., A Modular Luminescence Lifetime Imaging System for Mapping Oxygen Distribution in Biological Samples, Sensors and Actuators B, 1998, 51:163-170.

Holst, et al., Luminescence Lifetime Imaging With Transparent Oxygen Optodes, Sensors and Actuators B, 2001, 74:78-90.

Liebsch, et al., Luminescence Lifetime Imaging of Oxygen, pH, and Carbon Dioxide Distribution Using Optical Sensors, Applied Spectroscopy, 2000, 54(4):548-559.

Princeton Instruments, WinSpec Spectroscopic Software, Version 2.5K, Feb. 2, 2010, 276 pages.

Schroder, et al., Time-Resolved pH/pO2 Mapping With Luminescent Hybrid Sensors, Analytical Chemistry, 2007, 79(1):60-70.

Wang, et al., Optical Methods for Sensing and Imaging Oxygen: Materials, Spectroscopies and Applications, Chem. Soc. Rev., 2014, 43:3666-3761.

* cited by examiner

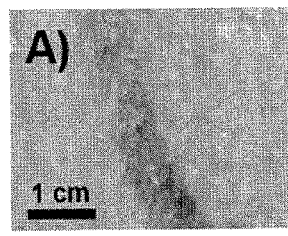 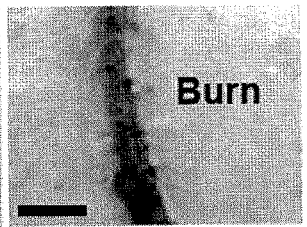 
FIG. 20A    FIG. 20B    FIG. 20C
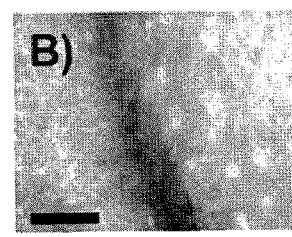  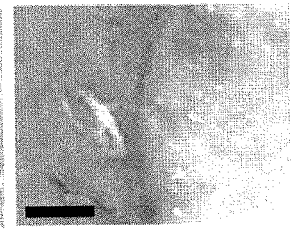
FIG. 21A    FIG. 21B    FIG. 21C
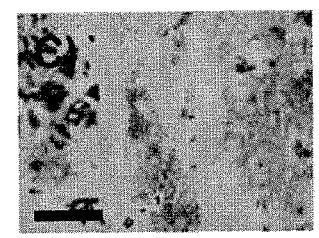 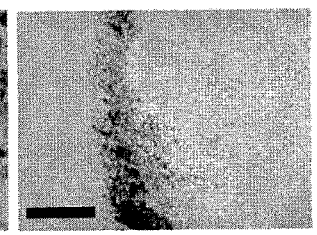 
FIG. 22A    FIG. 22B    FIG. 22C

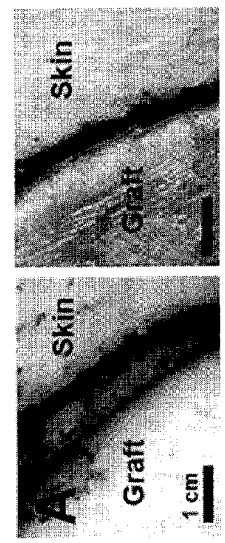
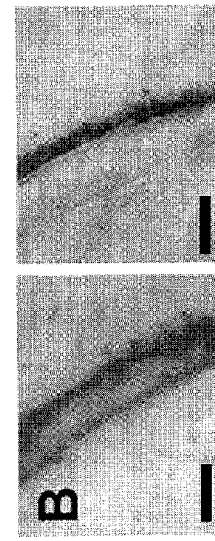
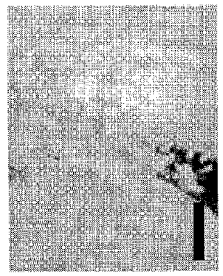
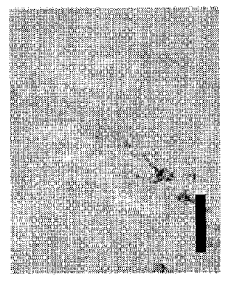
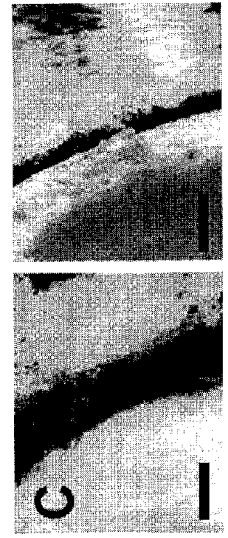

SYSTEM AND METHOD FOR PHOTOLUMINESCENCE DETECTION

CROSS-REFERENCE TO RELATED APPLICATIONS

This application represents the U.S. National Stage of International Application No. PCT/US2015/014065, filed Feb. 2, 2015 which is based on, claims the benefit of, and incorporates herein by reference, U.S. Provisional Patent Application Ser. No. 61/934,487, filed Jan. 31, 2014 and entitled "Rapid Image-based Determination of Phosphorescence Lifetime.

STATEMENT REGARDING FEDERALLY SPONSORED RESEARCH

Not applicable/This invention was made with government support under FA95501310068 awarded by the United States Air Force Office of Scientific Research. The government has certain rights in the invention.

BACKGROUND OF THE INVENTION

The disclosure relates, in general, to photoluminescence detection and, more particularly, a system and method for analyses based on phosphorescence lifetime measurements.

In a clinical setting, it is often desirable to monitor a patient's health by measuring tissue gas levels. Tissue-gas analyses are an essential part of modern patient care and are used in the diagnosis and treatment of a number of conditions. In particular, measurement of tissue oxygen concentration is heavily relied upon both for general monitoring of overall patient health and for treatment of specific conditions, such as ischemia, burns, and diabetic foot syndrome.

There are several approaches that may be used to perform blood and tissue gas analyses. Invasive approaches generally involve collecting and analyzing a blood sample drawn from an artery. While blood sample analysis may be performed within minutes and provide accurate results, testing may require a trained practitioner and careful sample handling or results may be inaccurate. Further, invasive testing may not be suitable for repeated analysis or long-term monitoring.

Measurements of tissue oxygen concentration may also be achieved non-invasively. For example, a pulse oximeter is a basic, non-invasive instrument that detects hemoglobin saturation by monitoring the reflectance or absorbance of incident light. By comparison, probe-based systems may be used to measure transcutaneous oxygen (TcpO2) with electrodes or optical sensor foil-based patches that are attached to the sample surface and read out non-invasively using a microscope. In one aspect, TcpO2 systems may require multi-point calibration with specially prepared, well-defined samples. Further, calibrations are generally performed prior to each monitoring period, when changing measuring sites, every four hours, or every time an electrode has been remembraned. In addition, conditions such as room lighting, temperature, and other factors may influence the accuracy of the measurement.

Accordingly, there is a need for ways to perform non-invasive measurements of tissue oxygen concentration that are fast, easily administered, and generally insensitive to the external environment.

SUMMARY OF THE INVENTION

The present invention overcomes the aforementioned drawbacks by providing a system and method for photoluminescence detection.

In accordance with one aspect of the present disclosure, a system includes a light source, a detector, and a controller in electrical communication with the light source and the detector. The controller is configured to execute a program stored in the controller to (i) trigger the light source to emit a first pulse of light for illumination of a target, the first pulse of light having a first pulse duration, (ii) actuate the detector after a first delay time following emission of the first pulse of light to begin detecting a first signal from the target for a first detection time, and (iii) repeat (i) and (ii) at least once, varying for each repetition at least one of the first pulse duration, the first delay time, and the first detection time.

In one aspect, in (iii) of the program, the light source is triggered to emit a second pulse of light having a second pulse duration different from the first pulse duration. Further, in (iii) of the program, the detector is actuated after a second delay time equal to the first delay time following emission of the second pulse of light to begin detecting a second signal from the target for a second detection time equal to the first detection time.

In another aspect, in (iii) of the program, the detector is actuated after a second delay time different from the first delay time. Further, the light source is triggered to emit a second pulse of light having a second pulse duration equal to the first pulse duration, and the detector is actuated for a second detection time equal to the first detection time.

In yet another aspect, in (iii) of the program, the detector is actuated for a second detection time different from the first detection time. Further, in (iii) of the program, the light source is triggered to emit a second pulse of light having a second pulse duration equal to the first pulse duration, and the detector is actuated after a second delay time equal to the first delay time.

In one aspect, the light source is an electronic flash unit. In another aspect, the light source includes at least one band-pass filter. In yet another aspect, the detector includes at least one of a complementary metal-oxide semiconductor (CMOS) camera, and a charge-coupled device (CCD) camera. In still another aspect, the target includes an oxygen sensing wound dressing. In a further aspect, the first signal includes a phosphorescence emission detectable by the detector. In another aspect, the controller is further configured to execute the program stored in the controller to (iv) calculate, based on (i) and (ii), a number of repetitions for acquiring a threshold signal from the target, and in (iii), repeat (i) and (ii) at least the number of repetitions calculated in (iv).

In accordance with another aspect of the present disclosure, a method includes a step (a) of triggering a light source to emit a first pulse of light for illumination of a target, the first pulse of light having a first pulse duration, a step (b) of actuating a detector after a first delay time following emission of the first pulse of light to begin detecting a first signal from the target for a first detection time, and a step (c) of repeating (a) and (b) at least once, varying for each repetition at least one of the first pulse lifetime, the first delay time, and the first detection time.

In one aspect, the step (c) of the method further includes triggering the light source to emit a second pulse of light having a second pulse duration different from the first pulse duration. The step (c) of the method further includes actuating the detector after a second delay time equal to the first delay time following emission of the second pulse of light to begin detecting a second signal from the target for a second detection time equal to the first detection time.

In another aspect, the step (c) of the method further includes actuating the detector after a second delay time different from the first delay time. The step (c) of the method further includes triggering the light source to emit a second pulse of light having a second pulse duration equal to the first pulse duration, and actuating the detector for a second detection time equal to the first detection time.

In yet another aspect, the step (c) of the method further includes actuating the detector for a second detection time different from the first detection time. The step (c) of the method further includes triggering the light source to emit a second pulse of light having a second pulse duration equal to the first pulse duration, and actuating the detector after a second delay time equal to the first delay time.

In one aspect, the method further includes a step (d) of determining a phosphorescence lifetime for at least one location on the target, and a step (e) of calculating, based on the phosphorescence lifetime, a partial pressure of oxygen ($pO_2$) for the at least one location on the target. In another aspect, the light source is an electronic flash unit. In yet another aspect, the light source includes at least one bandpass filter. In still another aspect, the detector includes at least one of a complementary metal-oxide semiconductor (CMOS) camera and a charge-coupled device (CCD) camera. In a further aspect, the target includes an oxygen sensing wound dressing. In another aspect, the first signal includes a phosphorescence emission detectable by the detector.

In accordance with yet another aspect of the present disclosure, a device includes a light source operable to emit a pulse of light a detector for detecting a phosphorescence emission signal, and a controller in electrical communication with the light source and the detector. The controller is configured to execute a program stored in the controller to, (i) trigger the light source to emit a first pulse of light for illumination of a target, the first pulse of light having a first pulse duration, (ii) actuate the detector after a first delay time following emission of the first pulse of light to begin detecting a first signal from the target for a first detection time, and (iii) repeat (i) and (ii) at least once, varying at least one of the first pulse duration, the first delay time, and the first detection time. The target is an oxygen sensing wound dressing comprising an oxygen sensitive phosphor molecule.

In one aspect, the controller is further configured to execute the program stored in the controller to (iv) calculate, based on (i) and (ii), a number of repetitions for acquiring a threshold signal from the target, and in (iii), repeat (i) and (ii) at least the number of repetitions calculated in (iv).

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A shows phosphorescence detection in the presence of 20% $O_2$, and FIG. 5B shows phosphorescence detection in the presence of 0% $O_2$. Scale bars represent 2 mm.

FIG. 8A shows luminescence detection with no delay following excitation, and FIG. 8B shows luminescence detection after a short (e.g., about 500 µs) delay following excitation.

FIG. 19A is a depiction of phosphorescence intensity for a tissue including a burn. FIG. 19B is a depiction of phosphorescence intensity for a control tissue without a burn. FIG. 19C is a depiction of phosphorescence lifetime for a tissue including a burn. FIG. 19D is a depiction of phosphorescence lifetime for a control tissue without a burn. FIGS. 19A and 19B correspond to the intensity scale showing the relationship between signal intensity (R/G) and percent $O_2$ consumption rate (% Con). FIGS. 19C and 19D correspond to the intensity scale showing the relationship between inverse phosphorescence lifetime (1/tau) and percent $O_2$ consumption rate (% Con). Scale bars represent 0.5 cm.

FIGS. 20A-20C are photographic images depicting tissue samples from a porcine burn model. FIG. 20A shows an image of an unburned control tissue sample. FIG. 20B shows an image of a burned tissue sample at day 0 post-burn. FIG. 20C shows an image of a burned tissue sample at day 7 post-burn. Scale bars represent 1 cm.

FIGS. 21A-21C are optical images depicting a fluorescence readout for the tissue samples of FIGS. 20A-20C. FIG. 21A shows a fluorescence readout for the unburned control tissue sample of FIG. 20A. FIG. 21B shows a fluorescence readout for the burned tissue sample of FIG. 20B at day 0 post-burn. FIG. 20C shows a fluorescence readout for the burned tissue sample of FIG. 20C at day 7 post-burn. Scale bars represent 1 cm.

FIGS. 22A-22C are optical images depicting a colorimetric readout representative of the percent oxygen consumption rate (% Con) for the tissue samples of FIGS. 20A-20C. FIG. 21A shows a colorimetric readout of % Con for the unburned control tissue sample of FIG. 20A. FIG. 21B shows a colorimetric readout of % Con for the burned tissue sample of FIG. 20B at day 0 post-burn. FIG. 20C shows a colorimetric readout of % Con for the burned tissue sample of FIG. 20C at day 7 post-burn. The intensity scale depicts the corresponding percent oxygen consumption rate. Scale bars represent 1 cm.

FIGS. 23A-23D are photographic images depicting tissue samples from a porcine burn model. FIG. 23A is an image of a tissue sample including a full thickness graft at day 0 post-graft. FIG. 23B is an image of a tissue sample including a partial thickness graft at day 0 post-graft. FIG. 23C is an image of a tissue sample including a full thickness graft at 1 month post-graft. FIG. 23D is an image of a tissue sample including a partial thickness graft at 1 month post-graft. Scale bars represent 1 cm.

FIGS. 24A-24D are optical images depicting a fluorescence readout for the tissue samples of FIGS. 23A-23D. FIG. 24A is a fluorescence image of the tissue sample of FIG. 23A including a full thickness graft at day 0 post-graft. FIG. 24B is a fluorescence image of the tissue sample of FIG. 23B including a partial thickness graft at day 0 post-graft. FIG. 24C is a fluorescence image of the tissue sample of FIG. 23C including a full thickness graft at 1 month post-graft. FIG. 24D is a fluorescence image of the tissue sample of FIG. 23D including a partial thickness graft at 1 month post-graft. Scale bars represent 1 cm.

FIGS. 25A-25D are optical images depicting a colorimetric readout representative of the percent oxygen consumption rate (% Con) for the tissue samples of FIGS. 23A-23D. FIG. 25A is a colorimetric readout of % Con for the tissue sample of FIG. 23A including a full thickness graft at day 0 post-graft. FIG. 25B is a colorimetric readout of $pO_2$ for the tissue sample of FIG. 23B including a partial thickness graft at day 0 post-graft. FIG. 25C is a colorimetric readout of % Con for the tissue sample of FIG. 23C including a full thickness graft at 1 month post-graft. FIG. 25D is a colorimetric readout of % Con for the tissue sample of FIG. 23D including a partial thickness graft at 1 month post-graft. The intensity scale depicts the percent oxygen consumption rate. Scale bars represent 1 cm.

DETAILED DESCRIPTION OF THE INVENTION

Figure 1:
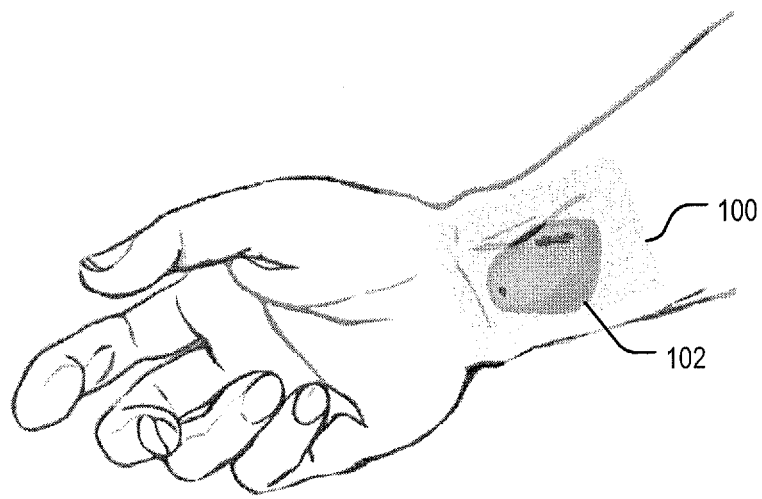
FIG. 1 is a schematic illustration of an embodiment of an oxygen sensing wound dressing applied to the right forearm of a patient.

The present invention is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention.

As also discussed above, in various situations it may be useful to provide a non-invasive technique for performing blood and tissue gas analyses. One method for sensing oxygen in biological or tissue environments includes oxygen-dependent quenching of phosphorescence. However, the acquisition of phosphorescence lifetime values can result in practical and technical limitations for deployment of phosphorescent oxygen sensors (i.e., oxygen sensitive phosphor molecules) to clinical and other non-laboratory environments. Typically, measurement of phosphorescence lifetime may include performing a series of independent, time-resolved intensity measurements through a technique known as phosphorescence lifetime analysis. In this approach, a short (i.e., less than about 1 µs) excitation pulse is delivered to a sample including a phosphorescent material. Photon counts incident upon a detector associated with the resulting phosphorescence decay signal produced by the phosphorescent material may be measured in a series of discretized time bins that group photon counts according to their arrival time at the detector. This method, which usually requires extensive averaging to make a reliable measurement at any given time point, may be time-consuming, involve specialized equipment, and rely upon specially trained operators. Further, the presence of a finite excitation pulse width may convolve the excitation pulse with the measured lifetime traces. As a result, the application of pulse width deconvolution to the acquired data may be required before further analysis can be performed. Various other challenges may arise as environmental factors are taken into account or as requirements for measurements become more exacting.

Use of the disclosed system and method for phosphorescence lifetime analysis may address these and other issues. In one aspect, the present disclosure provides a method to determine phosphorescence lifetime from a phosphor distributed across an arbitrary surface. The phosphor may be an oxygen sensitive phosphor molecule or another phosphor molecule. A system and method may include a camera, at least one flash or light source, and a controller or other device that provides a variable, time-delayed signal to synchronize the camera and light source. In one aspect, the camera may be a standard, commercially available wide-field camera, a complementary metal-oxide semiconductor (CMOS) camera, a charge-coupled device (CCD) camera, or the like. In another aspect, the light source may be an electronic flash unit, an assembly of one or more light emitting diodes (LEDs), or another suitable source of light. The light source may further include one or more band-pass filter to specify the wavelength(s) emitted by the light source. Embodiments of a method may include rapid alteration of the time delay between the onset of the flash pulse and the period at which the camera begins to acquire an image. Analyses of the acquired images may provide an accurate determination of the phosphorescence lifetime at any given pixel in the image or image series without the need for time binning, repeated averaging, or, in some embodiments, excitation pulse deconvolution. In one aspect, the system and method may facilitate deployment of phosphorescent lifetime-based sensors in a variety of end applications, including clinical and point-of-care medicine.

One aspect of the present disclosure includes a method for determining the phosphorescence lifetime of a phosphor contained within an imaged region through rapid, wide-field imaging and image analysis. Traditional methods for phosphorescence lifetime analysis may rely on time-resolved imaging in which the lifetime curve is reconstructed through piecewise, time-dependent analysis of individual, discretized regions of the phosphorescence lifetime curve. In contrast, embodiments of the present disclosure provide an approach that is capable of generating similar or identical information through analysis of one or more pixels in a series images. In one aspect, the images may be acquired using a standard or traditional wide-field camera.

In some embodiments, a system and method for determining phosphorescence lifetime includes a time-variable trigger signal that is capable of manipulating the delay between when the flash or light source is turned on and when the camera is actuated to acquire an image or signal. In one aspect, the flash pulse may completely dissipate prior to image acquisition, which may eliminate phosphor re-excitation during the image acquisition period along with related issues. In another aspect, autofluorescence, which has emission lifetimes several orders of magnitude faster than phosphorescence, may also confound analysis of phosphorescence lifetime. Accordingly, embodiments of a system and method may allow for autofluorescence to fully dissipate prior to image acquisition.

In some embodiments, a controller may be configured to actuate the camera or other detector to being detecting at an arbitrary point during the phosphorescence decay curve. Once the camera is actuated, a normal, fixed-length image acquisition cycle may be completed, thereby generating a phosphorescence intensity map of an imaged point or area on a target. In one aspect, the entire process may take about 20 milliseconds (ms), at which point the system may be ready to acquire another image. By sequentially varying the time-delay between triggering the flash and actuating the detector, a time-series of phosphorescence intensity images may be rapidly acquired. The intensity per pixel may be plotted and analyzed for all images in the series to calculate the phosphorescence lifetime at each point or pixel.

In some embodiments, the present disclosure provides the ability to determine accurate per-pixel phosphorescence lifetimes without the requirement of excitation pulse deconvolution. Further, lifetime data for a phosphor molecule may be determined through analysis of an image series acquired in the manner described above with the resulting data being comparable to lifetime data determined using traditional lifetime analysis.

In a non-limiting example, a phosphorescent molecule may be embedded in an oxygen sensing wound dressing, such as a polymer bandage matrix, and the dressing may be applied over a wound. Using an embodiment of a system including a light source, detector, and controller for providing a time-variable trigger signal, a series of phosphorescence intensity images of the dressing may be sequentially acquired, with the delay between triggering the light source and actuating the detector being varied in 0.1 ms intervals between each flash-detection cycle. About 10 to about 15 images may be acquired, and the entire image series may take less than about 10 seconds to complete. The phosphorescence intensities at each pixel may be determined from each image and aggregated. From this information, a per-pixel phosphorescence decay curve may be reconstructed and the phosphorescence lifetime may be calculated. This information may be used to assess the tissue underlying dressing. For example, the phosphorescence lifetime data may be correlated with or otherwise equated to a concentration or partial pressure of oxygen ($pO_2$) to determine tissue oxygenation.

In one aspect, a system and method according to the present disclosure may be applied to phosphorescence lifetime determination in laboratory or clinical settings. Further, image analysis algorithms, software, or the like may be provided for lifetime-based measurements in applications that include, but may not be limited to, clinical wound assessment, graft monitoring, burn depth analysis, perfusion, tissue oxygenation measurements, the like, and combinations thereof. Embodiments of the present disclosure may further provide calibration methodology for lifetime-based measurements of oxygen and other physiological parameters.

Figure 2:
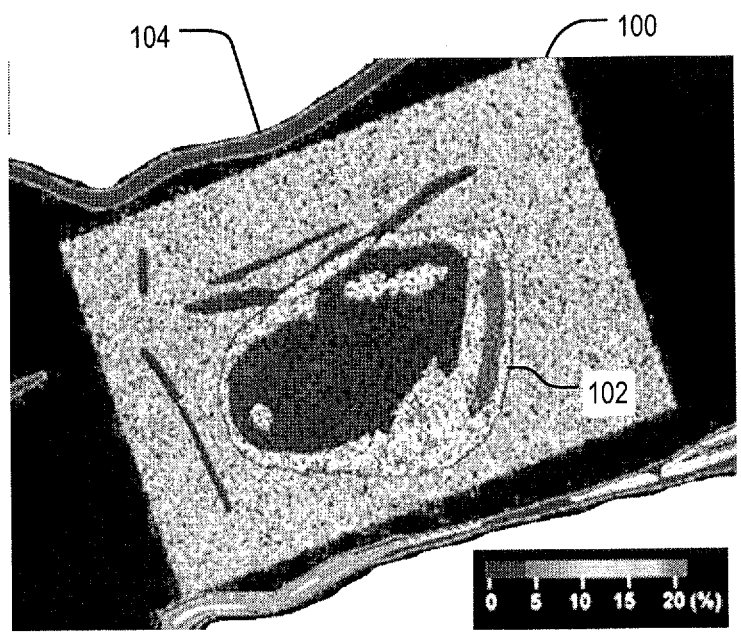
FIG. 2 is an enlarged partial view of the oxygen sensing wound dressing of FIG. 1 showing a colorimetric readout representative of oxygen concentration.

Turning now to the Figures, embodiments of the present disclosure may include a system, device or method for analyzing a target such as a dressing 100 shown in FIGS. 1 and 2. The dressing 100 may include a covering for application to a surface such as a surface of a body part of a patient. In the example illustrated in FIGS. 1 and 2, the dressing 100 is applied over a wound 102 on a forearm 104 of a subject. It will be appreciated that the term dressing may apply to various coverings, such as an ointment, gauze, solid or liquid covering, or the like. The terms dressing, bandage, covering and related terms may be used throughout the disclosure to refer to a dressing. Further examples of a dressing are described, for example, in WO 2014/011724 to Evans et al.

Figure 3:
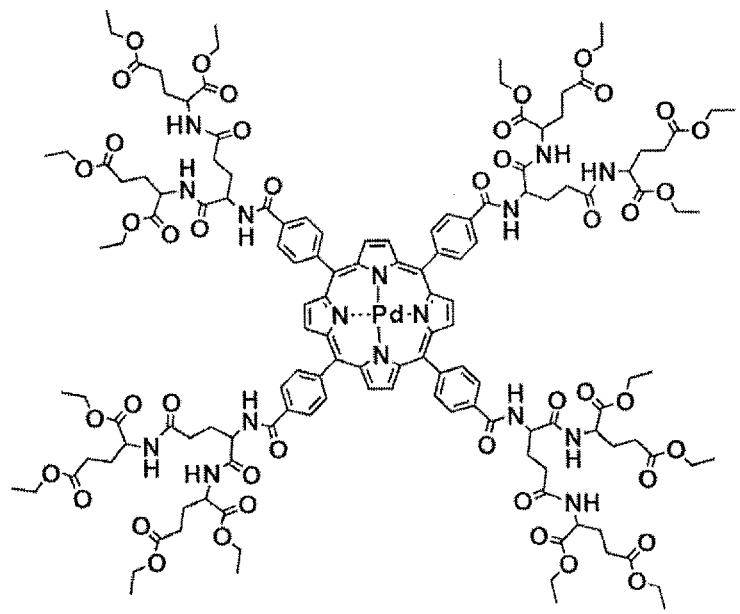
FIG. 3 is an illustration of a chemical structure for an example oxygen sensitive phosphor molecule for use with the wound dressing of FIG. 1.

With continued reference to the dressing 100, measurements of parameters, such as tissue parameters, may be made using one or more sensor elements 106, such as an oxygen sensitive phosphor molecule (see FIG. 3). The sensor elements 106 may not be in direct contact with a tissue, such as the wound 102. In one aspect, the sensor elements 106 may be contained, compartmentalized, or a combination thereof within the dressing 100, which may be in physical contact with an underlying tissue. Readout and quantification of tissue parameters may be made for species including, but not limited to, chromophores, fluorophores, or phosphors whose absorption or emission properties change based on their passive or active interaction with the tissue. The signal may be responsive to analytes within the tissue by modulation of inelastic scattering of an electromagnetic field, including such mechanisms as phosphorescence, fluorescence, absorption, and the like.

Figure 4:
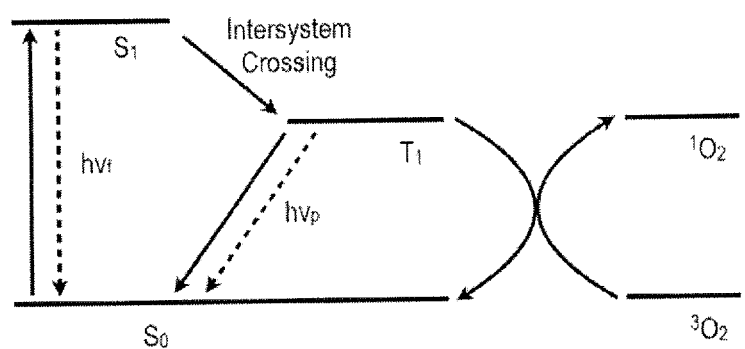
FIG. 4 is a simplified Jablonski diagram showing the deactivation pathways for a triplet-state emitter such as the oxygen sensitive phosphor molecule of FIG. 3.

In one aspect, it may be possible to alter and set the excited state lifetimes of the sensor elements 106. Excited states of a molecule may have intrinsic lifetimes during which the excited states can be populated. The lifetimes may be dependent on an array of parameters, including molecular structure, temperature, solvation condition, surrounding molecules, and chemical interactions to name a few. The lifetime of these states may be important in the development of sensor elements 106, such as in the case of oxygen sensing. For example, tissues in the body may contain molecules that are naturally fluorescent, such that exposure of tissue to certain wavelengths of light may lead to fluorescent emissions. The signal strength of these emissions may be larger or comparable to the emissions of some sensor elements. To separate the emission of the sensor elements 106 from fluorescence, it may be possible to chemically create a sensor element with an emissive excited state lifetime longer than the states of molecules who give rise to fluorescence emission. If a sensor element is created with a long-lived excited triplet state, and this triplet state leads to phosphorescence (see FIG. 4), then it may be possible to temporally distinguish the long-lived phosphorescence of a sensor element from the fluorescence of a sensor element. For example, the oxygen sensor element Oxyphor R2 has a maximum phosphorescence lifetime of almost 1 millisecond, a lifetime that is one thousand times longer than the longest tissue fluorescence source. By using a short temporal illumination (e.g., about 500 microseconds long) with a system including a camera or detector temporally gated or controlled to detect signals emitted at longer lifetimes (e.g., about 800 microseconds after a pulse of light) it may be possible to selectively detect only the phosphorescence without detecting the fluorescence signal.

In one aspect, one or more sensor elements 106 may be embedded or enmeshed within the dressing 100 or other compatible matrix that serves to modulate the sensitivity of the sensor elements 106, enhance the stability and useful lifetime of the sensor elements 106, or a combination thereof. In certain embodiments, the sensor elements 106 include a foam, hydrogel, polymer or mixture of multiple ingredients of uniform or variable porosity, or heterogeneous/asymmetric or homogeneous/symmetric dendrimeric structures or layers, or a combination thereof surrounding each individual sensor element 106.

Figure 5A:
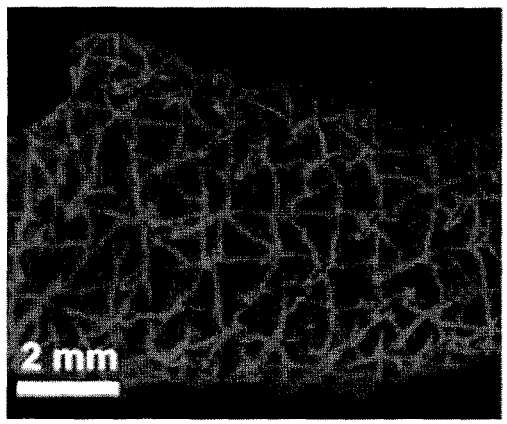
FIGS. 5A and 5B are optical images depicting a colorimetric readout associated with phosphorescence quenching of oxygen sensitive phosphor molecules in the presence of oxygen.
Figure 5B:
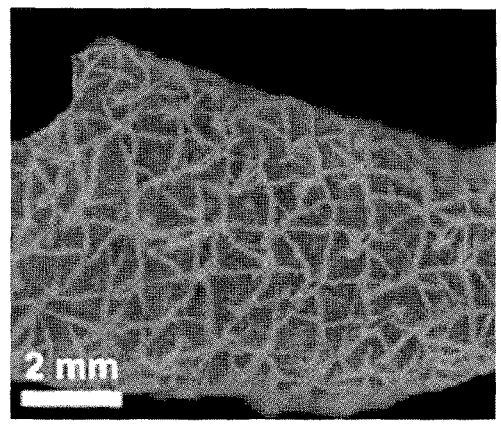

With reference to FIGS. 5A and 5B, a material including an oxygen sensitive phosphor molecule may provide a varied phosphorescence emission signal depending on the concentration of oxygen in the environment surrounding the oxygen sensitive phosphor. For example, a material including an oxygen sensitive phosphor molecule in the presence of about 20% $O_2$ (FIG. 5A) may provide a reduced phosphorescence emission signal as compared with the same material in the presence of about 0% $O_2$ (FIG. 5B). In terms of a colorimetric or signal intensity readout, a brighter signal (lighter appearance) may correspond to a greater phosphorescence emission signal and a lower concentration of $O_2$. By comparison, a dimmer signal (darker appearance) may correspond to a reduced phosphorescence emission signal and a greater concentration of $O_2$.

Figure 6:
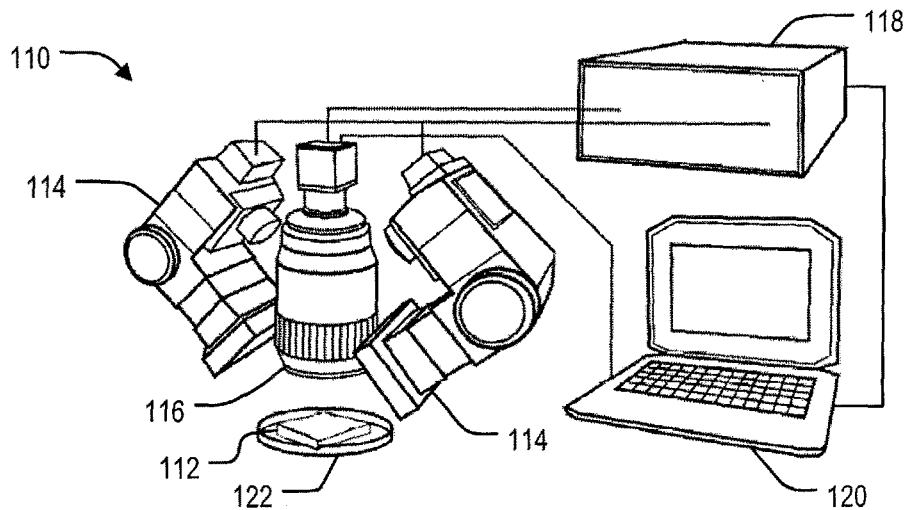
FIG. 6 is a schematic illustration of an example system for sensing oxygen including a light source, a detector, a controller, and an interface.

Turning now to FIG. 6, a system 110 for analyzing a target 112 may include a light source 114, a detector 116, and a controller 118. The controller 118 may be in electrical communication with the light source 114 and the detector 116. Further, the controller 118 may be configured to execute a program stored in the controller 118 to carry out one or more steps, actions or the like. The controller may also be physically contained within or merged with the body of a camera or handheld device. In one aspect, the system 110 may further include an interface 120 such as a computer with a keyboard and display unit as illustrated in FIG. 6. An interface may also be a tablet computer, a smartphone, or the like. The interface 120 may be in electrical (wired or wireless) communication with one or more of the light source 114, the detector 116, and the controller 118. Moreover, in some embodiments, two or more of the light source 114, the detector 116, the controller 118, and the interface 120 may be incorporated into a single hand-held device, table-top module, or the like. For example, a hand-held device can resemble a large pen or stylus. The device may include the light source 114, the detector 116, and the controller 118, and optionally, the interface 120.

In some embodiments, the target 112 may be a dressing such as the dressing 100. Accordingly, the target 112 may include one or more sensor elements 106, such as an oxygen sensitive phosphor molecule. The system 100 may include a stand or support 122 for containing or positioning the target 112 for analysis. However, in some embodiments, the target 112 may be positioned or otherwise disposed on another surface or location. For example, the target 112 may be a dressing applied to a tissue or wound of a subject or patient as shown in FIG. 1.

In some embodiments, the system 100 may include a single light source 114 or multiple (i.e., two or more) light sources 114. In the case of multiple light sources 114, the light sources 114 may be incorporated into a single device or housing, or the light sources 114 may be provided as separate devices as illustrated in FIG. 6. In one aspect, the light source 114 may be an electronic flash unit. In another aspect, the light source 114 may include or be equipped with one or more band-pass filters, polarizers, or the like. For example, a band-pass filter may be provided control the light source to selectively emit at a predetermined wavelength or band of light. The band-pass filters or other characteristics of the light source (e.g., the emission source) may be selected depending on the target 112, the oxygen sensing phosphor, a reference dye, the like, or combinations thereof.

In some embodiments, the system 100 may include a single detector 116 or multiple detectors 116. In one example, a detector may be a camera such as a wide-field camera, a CMOS camera configured for detection at a given wavelength or band of light (e.g., infrared, near infrared, visible, ultraviolet, and the like), a CCD camera, or the like. The detector 116 may further include one or more lenses, mirrors, filters, or the like, to collect a signal emitted from the target 112. For example, the detector 116 may include one or more band-pass filters for capturing different color channel images. In one aspect, the system 110 may include a mechanism for manually or automatically switching between different filters. In another aspect, a camera or other detector may include independent color channels, thereby potentially obviating the use of one or more filters.

With continued reference to FIG. 6, the light source 114 and the detector 116 may be in communication with and controlled by the controller 118. In one example, the controller 118 is a digital delay or pulse generator. The controller 118 may include one or more programs stored in the controller 118 to trigger the emission of a pulse of light or flash pulse from the light source 114 to illuminate or excite the target 112. Further, the controller 118 may include one or more programs stored in the controller 118 to actuate the opening of a camera shutter or other feature of the detector so that images or other signals may be acquired from the target 112. In one aspect, the controller 118 may actuate the detector 116 at a given time point after the light source 114 is triggered. Signal data or images acquired by the detector 118 may be received by the interface 120. The interface 120 may further be equipped to perform calculations, analyze data, perform image analysis, generate plots, graphs, reports, the like, or combinations thereof.

Figure 7:
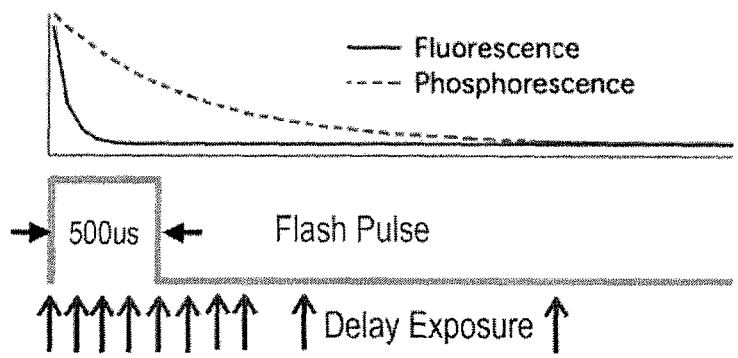
FIG. 7 is an example plot showing fluorescence and phosphorescence decay as a function of time for a corresponding light pulse.
Figures 8A, 8B:
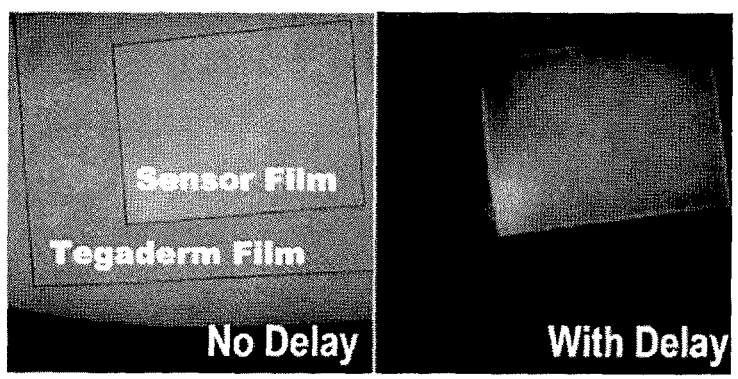
FIGS. 8A and 8B are optical images depicting a colorimetric readout associated with fluorescence and phosphorescence signals from an oxygen sensing wound dressing following excitation with a light pulse.
Figure 9:
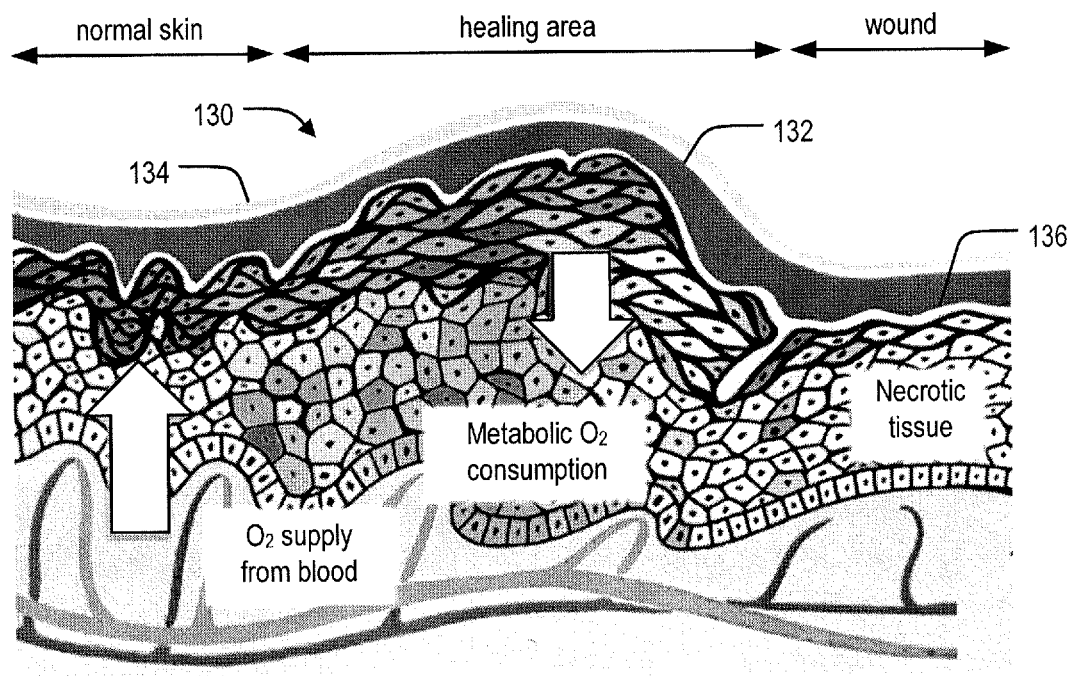
FIG. 9 is a schematic illustration showing the flow of oxygen for a partial cross-section of a tissue including a wound.

In one example, controller 118 may be configured to execute a program stored in the controller 118 to trigger the light source 114 to emit a pulse of light for illumination of the target 112. The pulse of light may have a predetermined or arbitrary pulse duration. The program may further actuate the detector 116 after a delay time following emission of the pulse of light to begin detecting a signal from the target 112 for a detection or acquisition time. An excitation-detection cycle (EDC) may include a combination of the program steps of triggering the light source 114 and actuating of the detector 116 as executed by the controller 118. With reference to FIG. 7, an EDC may include a pulse of light or flash pulse having a square profile as illustrated. However, other pulse profiles may be used. In one example, the pulse of light may have a pulse lifetime, pulse duration, or pulse width of 500 microseconds (μs). Actuation of the detector may occur beginning at any time starting before, during, or after the pulse of light is triggered as indicated by the vertical arrows in FIG. 7. In the case that the target 112 emits both a fluorescence and phosphorescence signal in response to excitation by the pulse of light, the detector 116 may detect either or both of the fluorescence and phosphorescence signals depending on when the detector is actuated as illustrated in the examples shown in FIGS. 8A and 8B. In one aspect, skin tissue beneath the Tegaderm film in FIG. 8A emits a fluorescence signal that may be acquired by the detector 116 when actuated with no delay following triggering of the pulse of light. However, if a delay is included between triggering the light source 114 and actuating the detector 116, the fluorescence signal from the skin tissue (target 112) is avoided and only the phosphorescence signal is observed as in FIG. 8B.

In some embodiments, the program may include a step or action of performing multiple EDCs. For example, the program may repeat the steps of triggering the light source 114 and actuating the detector 116 at least once. Further, for each EDC, the program may vary the pulse duration, the delay time, the detection time, or a combination thereof. In another example, the controller may be further configured to execute the program stored in the controller to calculate, based on the outcome of a first EDC, a number of repetitions for acquiring a threshold signal from the target 112. Based on the calculated number of repetitions, the program or controller may execute further EDCs up to and including the calculated number. Alternatively (or in addition), EDCs may be performed until the threshold signal from the target 112 achieved. In one aspect, a system and method may include at least 1 EDC. In one aspect, a system and method may include less than about 100 EDCs. In yet another aspect, the system and method may include between about 1 EDC and about 20 EDCs. In a further aspect, the system and method may include between about 2 EDC and about 10 EDCs.

In one aspect, the threshold signal may be the signal required to achieve an accurate determination of a characteristic of the target 112. In the case of measuring a phosphorescence emission signal from a dressing including an oxygen sensitive phosphor molecule, the threshold signal may be the aggregate or average signal required to achieve an accurate determination of phosphorescence decay lifetime for one or more points on the target 112 or pixels within an image acquired by the detector 116. Notably, the system 100 can be calibrated using a variety of methods include both known methods such as phosphorescence intensity, as well as methods according to the present disclosure.

Figure 10:
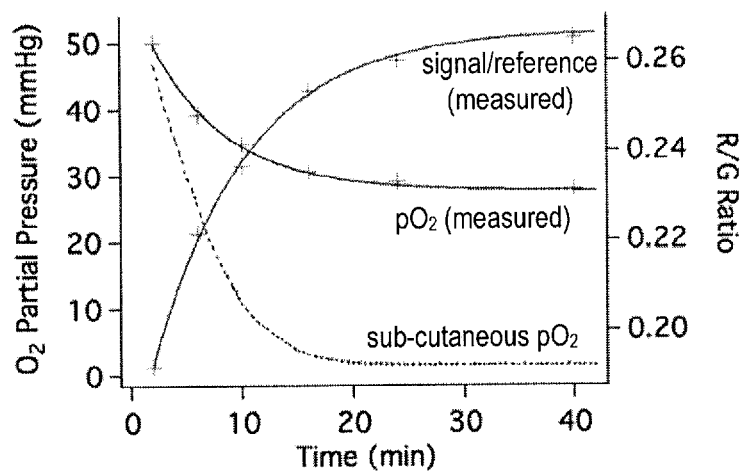
FIG. 10 is a dual-axis plot of both oxygen partial pressure (left vertical axis) and signal ratio (right vertical axis) for an oxygen sensitive phosphor relative to a reference dye as a function of time.

Turning now to FIGS. 9-18, an example is provided for a dressing 130 including a sensing layer 132 and a barrier layer 134. The sensing layer 132 may include an oxygen sensitive phosphor and an oxygen insensitive fluorophore as a reference. The sensing layer 132 may further include a polymer matrix material as a carrier for the fluorophores. In one aspect, the sensing layer 132 may be painted or otherwise applied to a tissue 136 in a liquid or liquid spray form. The tissue may include one or more regions such as a normal or healthy skin region, a healing region, and a wound region. Thereafter, the sensing layer 132 may dry or cure. The barrier layer 134 may be an optically transparent material. The barrier layer 134 layer may be applied concomitantly with the sensing layer 132 or applied sequentially. As shown in FIG. 10, the dressing 130 may be analyzed using known methods or methods according to the present disclosure to determine a signal (R) to reference (G) ratio, and therefore the concentration of oxygen over time as the tissue-dressing system reaches equilibrium.

Figure 11:
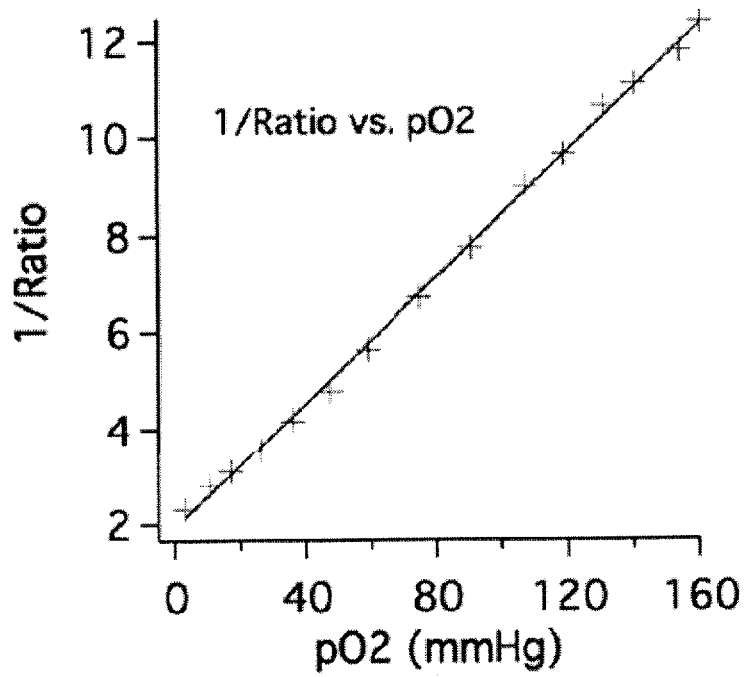
FIG. 11 is a plot of inverse signal ratio (i.e., reference dye/oxygen sensitive phosphor) as a function of oxygen partial pressure ($pO_2$).
Figure 12:
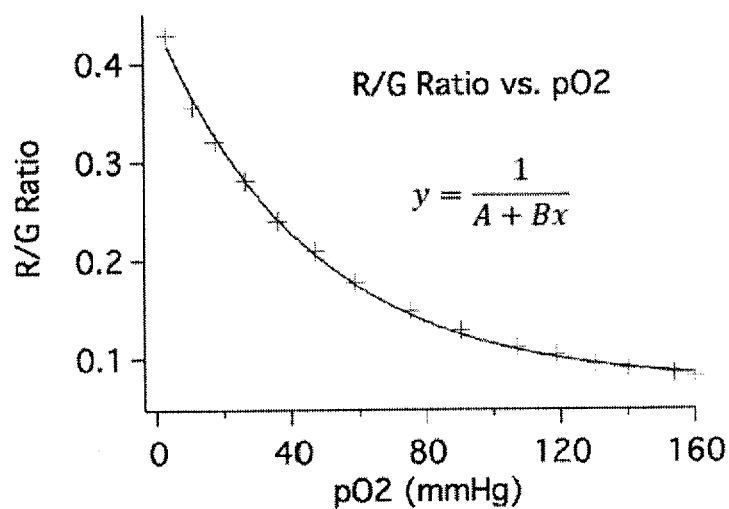
FIG. 12 is a plot of signal ratio (i.e., oxygen sensitive phosphor/reference dye) as a function of oxygen partial pressure ($pO_2$).

Referring to FIGS. 11 and 12, one known method for determining oxygen concentration based on a phosphorescence signal is based on intensity measurements. In one aspect a signal from an oxygen sensitive phosphor (R or Red signal) may be compared with a signal from the reference phosphor (G or Green Signal). A calibration curve may be constructed by plotting the R/G ratio at known oxygen concentrations or partial pressures ($pO_2$). In one aspect, the Intensity (I) of the phosphorescence emission may be related to $pO_2$ by the Stern-Volmer relationship as shown in Equation 1 (FIG. 12):

$$I = \frac{1}{\frac{1}{I_0} + K_q \times pO_2} \qquad \text{(Eq. 1)}$$

where $I_0$ is the intensity at 0% $O_2$ (i.e., no quencher), and $K_q$ is a constant (quencher rate coefficient). Rearranging Equation 1 for inverse intensity, the Stern-Volmer relationship may be given by Equation 2:

$$\frac{1}{I} = \frac{1}{I_0} + K_q \times pO_2 \qquad \text{(Eq. 2)}$$

which results in a linear relationship to $pO_2$ (FIG. 11). Turning now to FIGS. 13-16, a method for calculating $pO_2$ according to the present disclosure may use a phosphorescence decay or lifetime approach.

Figure 13:
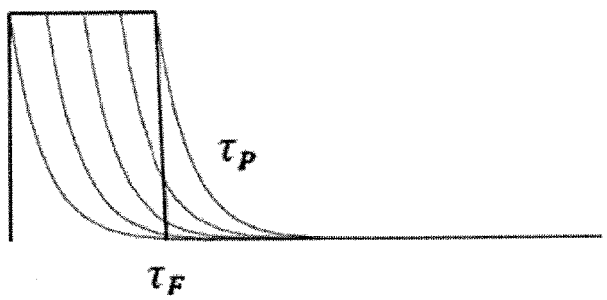
FIG. 13 is a plot of signal intensity as a function of time for a square light excitation pulse and corresponding phosphorescence decay curves.

With reference to FIG. 13, for a pulse of light having a pulse or flash duration ($\tau_F$), the corresponding phosphorescence decay lifetime ($\tau_P$) may be related to the instantaneous phosphorescence intensity ($I_P$) by the Equation 3:

$$I_P = I_0 e^{-t/\tau_P} \qquad \text{(Eq. 3)}$$

where t is the measurement time relative to a pulse of light at time t=0. For a pulse of light (flash excitation) having a finite pulse width ($\tau_F$), the instantaneous phosphorescence intensity is given by Equation 4:

$$I_P = I_0 e^{-(t-x)/\tau_P} \qquad \text{(Eq. 4)}$$

where $0 \leq x \leq \tau_F$, and x is the duration of the pulse of light. In one aspect the Equations 3 and 4 represent the general shape of phosphorescence decay following excitation.

Figure 14:
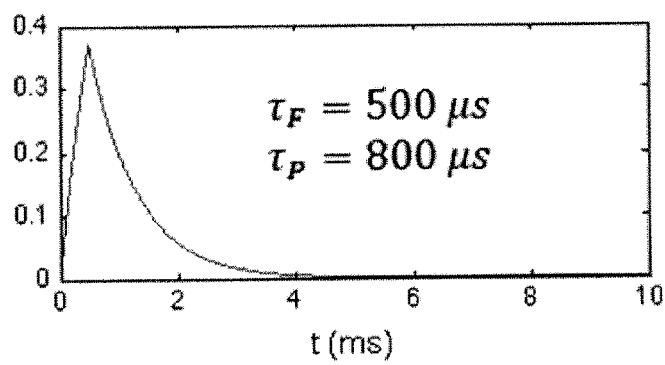
FIG. 14 is a plot of signal intensity as a function of time showing a theoretical phosphorescence signal response convolved with a square wave light excitation pulse between time 0 µs and 500 µs.
Figure 15:
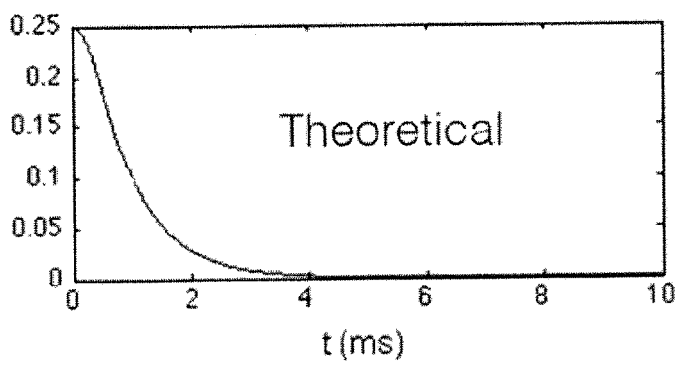
FIG. 15 is a plot of camera captured phosphorescence intensity as a function of camera shutter delay time, showing a theoretical camera captured intensity for a square wave light excitation pulse between time 0 µs and 500 µs.
Figure 16:
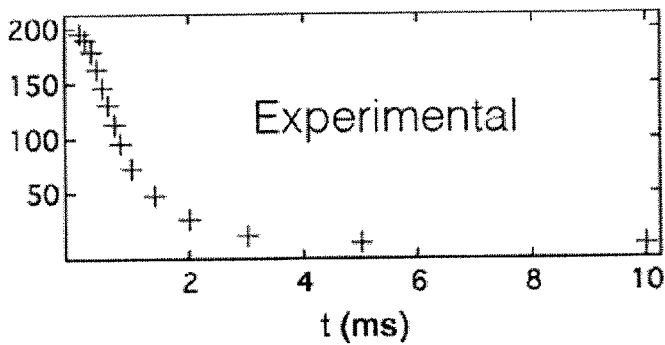
FIG. 16 is a plot of camera captured phosphorescence intensity as a function of camera shutter delay time, showing experimental data collected for camera captured intensity analogous to FIG. 15.
Figure 17:
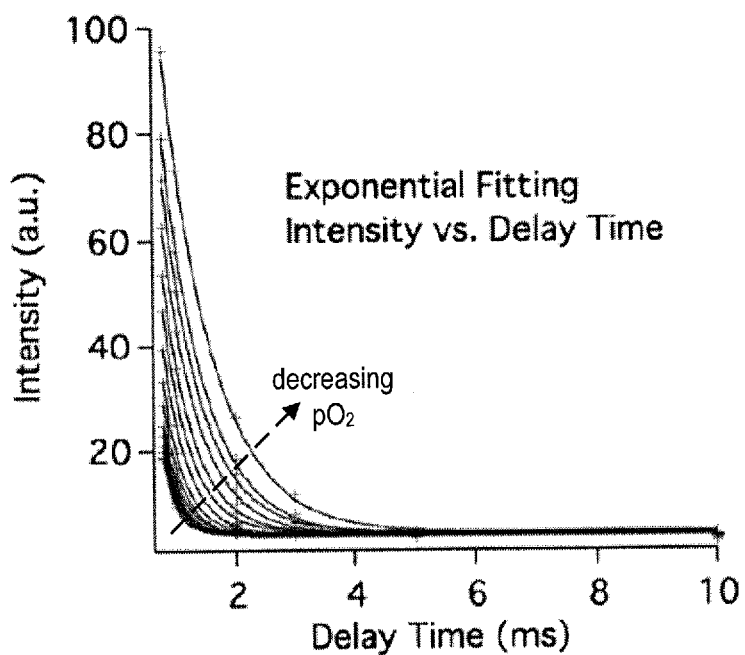
FIG. 17 is a plot of signal intensity as a function of time similar to that of FIG. 16 showing exponential fitting of several data sets collected across a range of $pO_2$ values. The value of $pO_2$ decreases for curves that are further from the origin as indicated by the dashed arrow.
Figure 18:
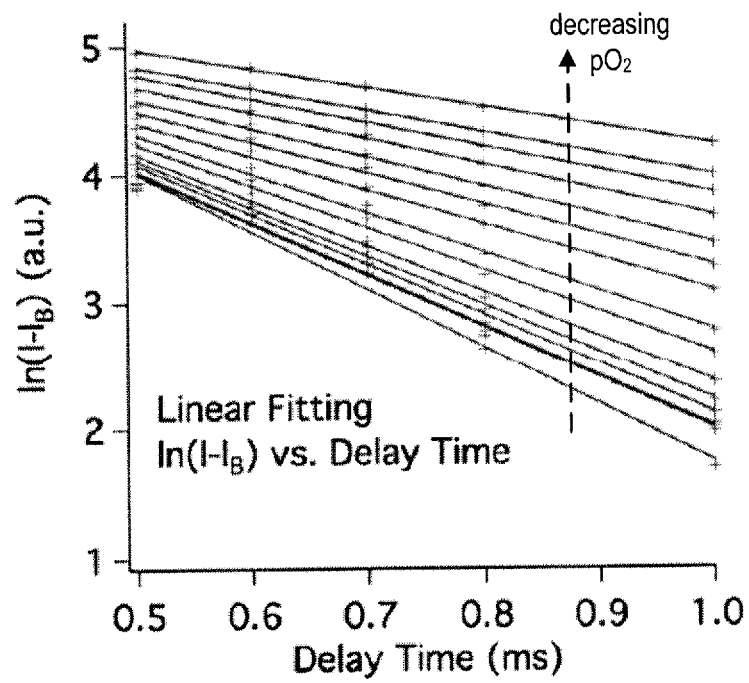
FIG. 18 is a plot of the log of signal intensity as a function of time showing linear fitting of the data shown in FIG. 17. The value of $pO_2$ decreases for curves that are further from the origin as indicated by the dashed arrow.
Figure 19A:
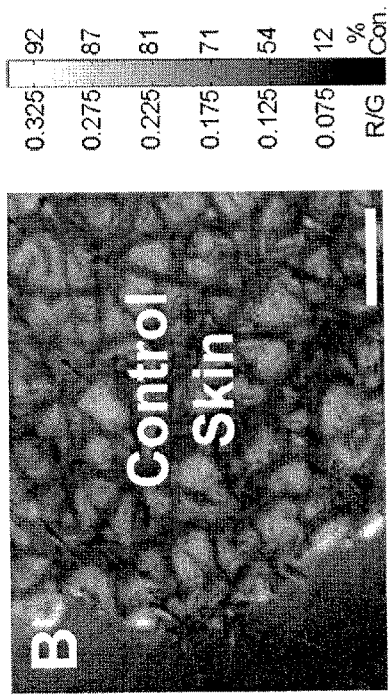
FIGS. 19A-19D are optical images depicting a colorimetric readout associated with phosphorescence quenching of oxygen sensitive phosphor molecules in the presence of oxygen.
Figure 19B:
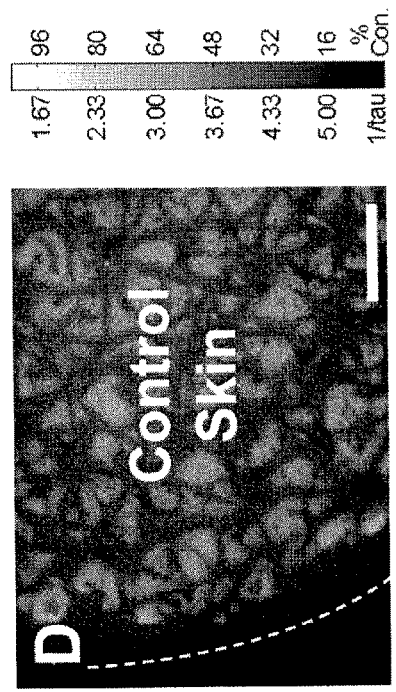
Figure 19C:
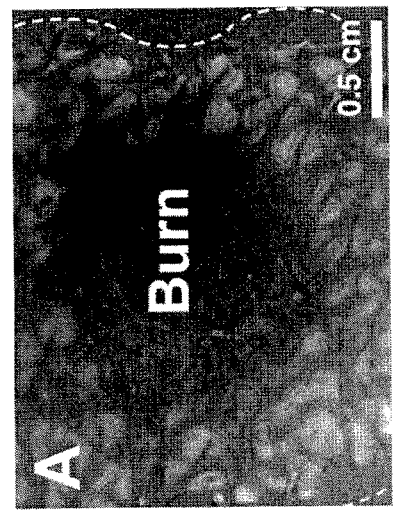
Figure 19D:
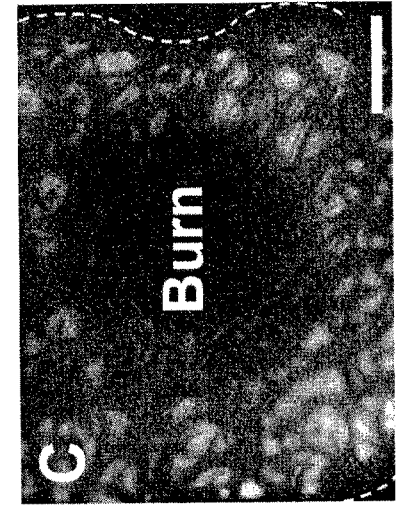

Turning to FIG. 14, the phosphorescence intensity as a function of time for times less than or equal to the pulse duration is given by Equation 5:

$$I(t) = \int_0^t I_0 e^{-(t-x)/\tau_P} dx = I_0 \tau_P (1 - e^{-t/\tau_P}) \quad \text{(Eq. 5)}$$

where $t \leq \tau_F$. However, the phosphorescence as a function of time for times greater than the pulse duration is given by Equation 6:

$$I(t) = \int_0^{\tau_F} I_0 e^{-(t-x)/\tau_P} dx = I_0 \tau_P (e^{\tau_F/\tau_P} - 1) e^{-t/\tau_P} \quad \text{(Eq. 6)}$$

where $t > \tau_F$. As shown in FIG. 14, for an example pulse duration of $\tau_F = 500$ μs and an estimated phosphorescence decay lifetime of $\tau_P = 800$ μs, the intensity (y-axis) increases sharply and then decays according to the equations above. Integrating Equation 5 for time out to infinity (in the case that the detector is continuously open) yields Equation 7:

$$I_d(t) = \int_t^{\tau_F} I_0 \tau_P (1 - e^{-t/\tau_P}) dt + \quad \text{(Eq. 7)}$$
$$= \int_{\tau_F}^{\infty} I_0 \tau_F (e^{\tau_F/\tau_P} - 1) e^{-t/\tau_P} dt$$
$$= I_0 \tau_F (\tau_F + \tau_P - t) - I_0 \tau_F \tau_P e^{-t/\tau_P}$$

for $t \leq \tau_F$. Similarly, integrating Equation 6 yields Equation 8:

$$I_d(t) = \int_t^{\infty} I_0 \tau_P (e^{\tau_F/\tau_P} - 1) e^{-t/\tau_P} dt = I_0 \tau_F \tau_P (e^{\tau_F/\tau_P} - 1) e^{-t/\tau_P} \quad \text{(Eq. 8)}$$

for $t > \tau_F$. The theoretical phosphorescence decay behavior (FIG. 15) with t=0 defined by the time when the detector is actuated (e.g., following a delay after the pulse of light) was determined to correlate well with data acquired experimentally (FIG. 16).

Considering only times after the pulse of light (i.e., $t > \tau_F$), Equation 8 may be rearranged to enable either exponential (FIG. 17) or linear (FIG. 18) fitting of phosphorescence lifetime data. Exponential fitting of measured data (in the form $y = A + Be^{-x}$) is shown in Equation 9:

$$I = I_B + I_0' e^{-t/\tau_P} \quad \text{(Eq. 9)}$$

where $I_B$ is the background intensity and $I_0'$ is given by Equation 10:

$$I_0' = I_0 \tau_F \tau_P (e^{\tau_F/\tau_P} - 1) \quad \text{(Eq. 10)}$$

Linear fitting can be achieved by rearranging to give Equation 11:

$$\ln(I - I_B) = \ln I_0' - \frac{t}{\tau_P} \quad \text{(Eq. 11)}$$

Turning now to FIGS. 19A-19D, a comparison of an example implementation of a method according to the present disclosure with an intensity-based method illustrates that the present method may provide comparable results with known methods. Notably, the images acquired using the present method (FIGS. 19C and 19D) provided accurate per-pixel phosphorescence lifetimes as in FIGS. 19A and 19B.

Further examples of application of the present method are illustrated in FIGS. 20A-25D. For example, FIGS. 20A-22C illustrate that embodiments of a method according to the present disclosure may provide oxygenation related data for an oxygen sensitive wound dressing applied to burned and unburned tissue. In one aspect, the data may be used to understand tissue oxygenation over a period of time. The data may include oxygen consumption data, $pO_2$ data, or the like. In another aspect, FIGS. 23A-25D illustrate that the present disclosure may provide oxygenation related data for an oxygen sensitive wound dressing applied to full thickness and partial thickness skin grafts.

Figure 26:
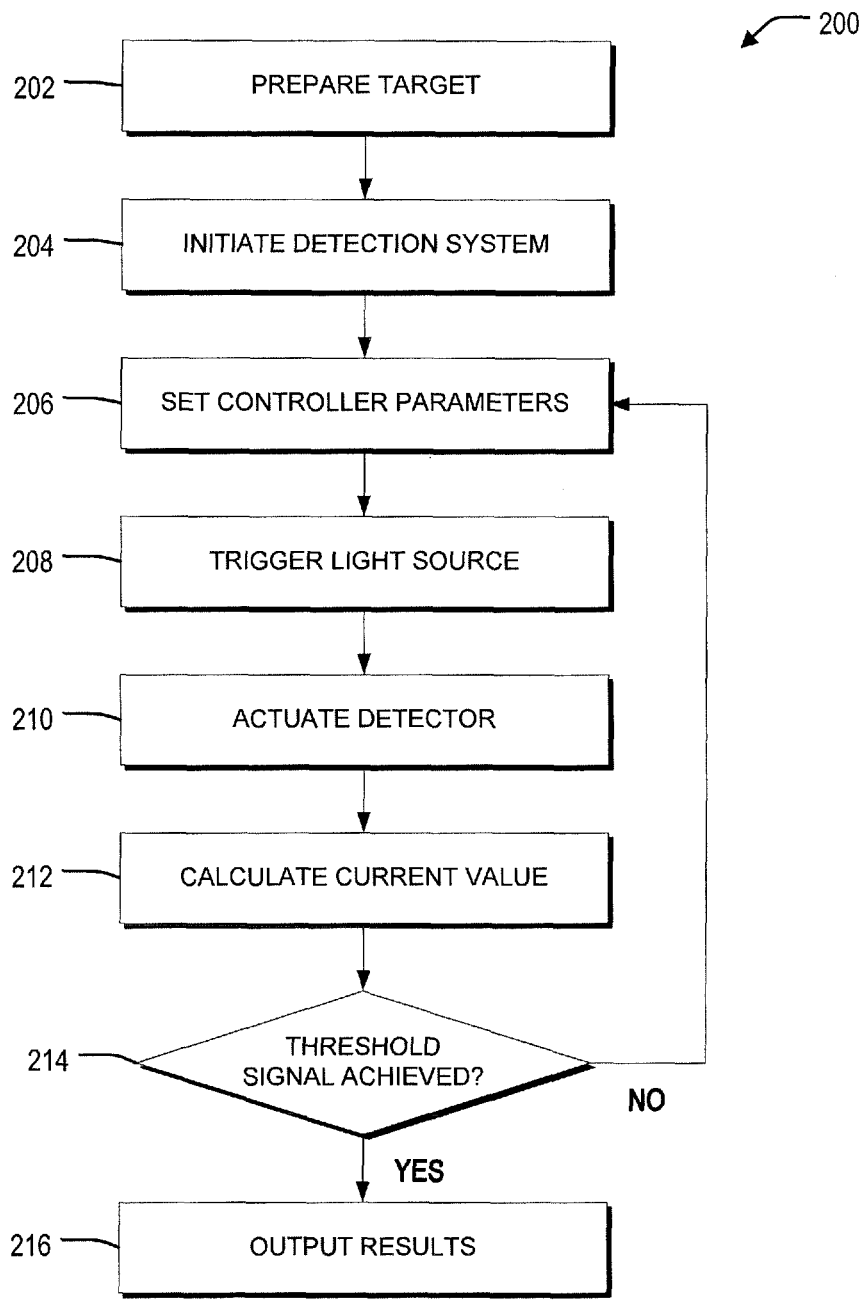
FIG. 26 is a schematic illustration of an example method for analysis of a target including a sensor element.

Turning now to FIG. 26, a method 200 according to the present disclosure may include a step 202 of preparing a target, which may include a dressing, bandage, or other sensing system. The step 202 may include mixing an oxygen sensitive phosphor with a matrix material for application to a tissue or other surface, application of a dressing including a sensor element to a tissue or other surface, cleaning or equilibrating an applied dressing, or the like. Accordingly, the step 202 may include any suitable preparation or application of a target or the like for subsequent analysis with embodiments of a system according to the present disclosure.

In a step 204 of the method 200, a user or operator may initiate a detection system. In one aspect the detection system may be similar to or the same as the system 100 illustrated in FIG. 6. Initiation of the system may include powering on, equilibrating, connecting, or otherwise readying the system for use, including analysis of a dressing or other target. The method 200 may further include a step 206 of setting controller parameters. The step 206 may be performed manually by an operator of the system or automatically by the system itself. In one aspect, the user may interface with the system to indicate that the system should set the control parameters. In another aspect, the user may be provided with a prompt to input or select from a list or range of parameters. In still another aspect, the system may automatically set controller parameters based on sensed conditions or environmental characteristics (e.g., external light intensity, temperature, humidity, or the like), base on factory or user specified parameters, or the like. Examples of controller parameters may include pulse duration, delay time, detection time, threshold value, or other suitable parameters.

In a step 208 of the method 200, the user, the system, or the controller may execute a program stored in the controller to trigger a light source. The light source may be triggered to emit a first pulse of light for illumination of the target. The first pulse of light may have a pulse duration. In one aspect, the pulse duration may be between about 1 μs and about 1 minute. In another aspect, the pulse duration may be at least about 1 μs. In yet another aspect, the pulse duration may be less than about 1 second. In one particular embodiment, the pulse duration may be between about 100 μs and about 900 μs.

The method 200 may further include a step 210 including actuating a detector. The user, the system, or the controller may execute a program stored in the controller to actuate the detector. Further, the detector may be actuated after a delay time following emission of the pulse of light in the step 208 to begin detecting a signal from the target for a detection time. In one aspect, the delay time may be between about 1 µs and about 1 minute. In another aspect, the delay time may be at least about 1 µs. In yet another aspect, the delay time may be less than about 1 second. In one particular embodiment, the delay time may be between about 10 µs and about 900 µs. In other embodiments, the delay time may be omitted (i.e., the delay time is zero). In one aspect, the detection time may be between about 1 µs and about 1 minute. In another aspect, the detection time may be at least about 1 µs. In yet another aspect, the detection time may be less than about 1 seconds. In one particular embodiment, the detection time may be between about 10 µs and about 900 µs.

In a step 212 of the method 200, the system may calculate a current value. In one aspect, the current value may be an aggregate or average value, a standard error or deviation, or another measure of the quality or quantity of the data (e.g., signal intensity) acquired. In another aspect, the current value may be referenced to threshold signal. As described above, the threshold signal may relate to, for example, a number of acquisition cycles or EDCs to perform to achieve a given objective. In one example, after performing a first EDC that includes at least the step 208 and the step 210, the system may calculate a current value. In another example, the system may average or otherwise aggregate that data acquired from each of the previous EDCs to provide the current value. Notably, the method 200 may include any number of EDCs. For example, the method 200 may include between about 1 and about 20 EDCs. In a step 214 of the method 200, the current value may be compared to a threshold signal. If the current value is less than the threshold value, then the method may proceed to the step 206. In one example, after performing a first acquisition cycle that includes at least the step 208 and the step 210, the system may calculate that a threshold signal can be achieved after about 10 acquisition cycles. In another example, the threshold value or cycle number may be specified by the user or determined based on another input. Accordingly, in some embodiments, the step 214 may be omitted with the method 200 simply performing the step 206 through the step 212 based on the calculated number of cycles.

If the threshold signal is achieved in the step 214 (e.g., the current value is greater than or equal to the threshold signal), then the method 200 may proceed to a step 216. In the step 216, results, data, images, or other information may be provided as an output receivable by a component of the system or an external component. For example, the results may be receivable by a memory unit such as a hard drive or flash memory device, or a processing unit such as a desktop computer, tablet, or other computation device. In another example, the system may include one or more processors, software programs, or other analytical components for rendering the results on an interface, display, or the like. Notably the method 200 may include simultaneous collection and data output. Other variations may also fall within the scope of the method 200.

The schematic flow chart shown in FIG. 26 is generally set forth as a logical flow chart diagram. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in FIG. 26 are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention has been described in terms of one or more preferred embodiments, and it should be appreciated that many equivalents, alternatives, variations, and modifications, aside from those expressly stated, are possible and within the scope of the invention.

Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

What is claimed is:

1. A system, comprising: a light source; a detector; and a controller in electrical communication with the light source and the detector, the controller configured to execute a program stored in the controller to: (i) trigger the light source to emit a first pulse of light for illumination of a target, the first pulse of light having a first pulse duration; (ii) actuate the detector after a first delay time following emission of the first pulse of light to begin detecting a first signal from the target for a first detection time; and (iii) repeat (i) and (ii) at least once, varying for each repetition at least one of the first pulse duration, the first delay time, and the first detection time, the controller further configured to output the detected signal, pulse duration, delay time, and detection time from each repetition to a computational device, the computational device configured to utilize the detected signal, pulse duration, delay time, and detection time from each repetition to calculate a background intensity component and a decay component.

2. The system of claim 1, wherein in (iii) of the program, the light source is triggered to emit a second pulse of light having a second pulse duration different from the first pulse duration.

3. The system of claim 2, wherein in (iii) of the program, the detector is actuated after a second delay time equal to the first delay time following emission of the second pulse of light to begin detecting a second signal from the target for a second detection time equal to the first detection time.

4. The system of claim 1, wherein in (iii) of the program, the detector is actuated after a second delay time different from the first delay time.

5. The system of claim 4, wherein in (iii) of the program, the light source is triggered to emit a second pulse of light having a second pulse duration equal to the first pulse duration, and wherein the detector is actuated for a second detection time equal to the first detection time.

6. The system of claim 1, wherein in (iii) of the program, the detector is actuated for a second detection time different from the first detection time.

7. The system of claim 6, wherein in (iii) of the program, the light source is triggered to emit a second pulse of light having a second pulse duration equal to the first pulse duration, and wherein the detector is actuated after a second delay time equal to the first delay time.

8. The system of claim 1, wherein the light source is an electronic flash unit.

9. The system of claim 1, wherein the light source includes at least one band-pass filter.

10. The system of claim 1, wherein the detector includes at least one of a complementary metal-oxide semiconductor (CMOS) camera, and a charge-coupled device (CCD) camera.

11. The system of claim 1, wherein the system further comprises the target and the target includes an oxygen sensing wound dressing.

12. The system of claim 1, wherein the detector is configured to detect a phosphorescence emission from the first signal.

13. The system of claim 1, wherein the controller is further configured to execute the program stored in the controller to (iv) calculate based on (i) and (ii), a number of repetitions for acquiring a threshold signal from the target, and in (iii), repeat (i) and (ii) at least the number of repetitions calculated in (iv).

14. A method, comprising: (a) triggering a light source to emit a first pulse of light for illumination of a target, the first pulse of light having a first pulse duration; (b) actuating a detector after a first delay time following emission of the first pulse of light to begin detecting a first signal from the target for a first detection time; (c) repeating (a) and (b) at least once, varying for each repetition at least one of the first pulse duration, the first delay time, and the first detection time, and (d) utilizing the detected signal, pulse duration, delay time, and detection time from each repetition to calculate a background intensity component and a decay component.

15. The method of claim 14, wherein (c) of the method further includes triggering the light source to emit a second pulse of light having a second pulse duration different from the first pulse duration.

16. The method of claim 15, wherein (c) of the method further includes actuating the detector after a second delay time equal to the first delay time following emission of the second pulse of light to begin detecting a second signal from the target for a second detection time equal to the first detection time.

17. The method of claim 14, wherein (c) of the method further includes actuating the detector after a second delay time different from the first delay time.

18. The method of claim 17, wherein (c) of the method further includes triggering the light source to emit a second pulse of light having a second pulse duration equal to the first pulse duration, and actuating the detector for a second detection time equal to the first detection time.

19. The method of claim 14, wherein (c) of the method further includes actuating the detector for a second detection time different from the first detection time.

20. The method of claim 19 wherein (c) of the method further includes triggering the light source to emit a second pulse of light having a second pulse duration equal to the first pulse duration, and actuating the detector after a second delay time equal to the first delay time.

21. The method of claim 14, further including: (d) determining a phosphorescence lifetime for at least one location on the target, and (e) calculating, based on the phosphorescence lifetime, a partial pressure of oxygen ($pO_2$) for the at least one location on the target.

22. The method of claim 14, wherein the light source is an electronic flash unit.

23. The method of claim 14, wherein the light source includes at least one band-pass filter.

24. The method of claim 14, wherein the detector includes at least one of a complementary metal-oxide semiconductor (CMOS) camera and a charge-coupled device (CCD) camera.

25. The method of claim 14, wherein the target includes an oxygen sensing wound dressing.

26. The method of claim 14, wherein the detector is configured to detect a phosphorescence emission from the first signal.

27. A device, comprising: a light source configured to emit a pulse of light; a detector for detecting a phosphorescence emission signal; and a controller in electrical communication with the light source and the detector, the controller configured to execute a program stored in the controller to: (i) trigger the light source to emit a first pulse of light for illumination of a target, the first pulse of light having a first pulse duration; (ii) actuate the detector after a first delay time following emission of the first pulse of light to begin detecting a first signal from the target for a first detection time; and (iii) repeat (i) and (ii) at least once, varying at least one of the first pulse duration, the first delay time, and the first detection time, wherein the target is an oxygen sensing wound dressing comprising an oxygen sensitive phosphor molecule, the controller further configured to output the detected signal, pulse duration, delay time, and detection time from each repetition to a computational device, the computational device configured to utilize the detected signal, pulse duration, delay time, and detection time from each repetition to calculate a background intensity component and a decay component.

28. The device of claim 27, wherein the controller is further configured to execute the program stored in the controller to (iv) calculate, based on (i) and (ii), a number of repetitions for acquiring a threshold signal from the target, and in (iii), repeat (i) and (ii) at least the number of repetitions calculated in (iv).

* * * * *